United States Patent [19]
Schmidt et al.

[11] Patent Number: 6,114,527
[45] Date of Patent: Sep. 5, 2000

[54] PROCESS FOR PREPARING SUBSTITUTED PYRIMIDINE DERIVATIVES

[75] Inventors: Beat Schmidt, Baltschieder; Gerhard Stucky, Brig-Glis, both of Switzerland

[73] Assignee: Lonza AG, Gampel/Valais, Switzerland

[21] Appl. No.: 09/341,540

[22] PCT Filed: Jan. 8, 1998

[86] PCT No.: PCT/EP98/00074

§ 371 Date: Dec. 17, 1999

§ 102(e) Date: Dec. 17, 1999

[87] PCT Pub. No.: WO98/30549

PCT Pub. Date: Jul. 16, 1998

[30] Foreign Application Priority Data

Jan. 13, 1997 [CH] Switzerland ................. 55/97

[51] Int. Cl.$^7$ ................................................. C07D 239/02
[52] U.S. Cl. ............................................................ 544/319
[58] Field of Search ............................................... 544/319

[56] References Cited

FOREIGN PATENT DOCUMENTS 336250  3/1989  European Pat. Off. .
1806867 5/1970  Germany .

OTHER PUBLICATIONS

Gold, Angew. Chem, vol. 72, Ab. 24 (1960) pp 956–959.
Hoffman et al, J. of Organic Chemistry vol. 27, pp 551–8 (1962).
Bredereck et al, Chemische Berichte vol. 98, pp 3883–7 (1965).

Primary Examiner—John M. Ford
Attorney, Agent, or Firm—Fisher, Christen & Sabol

[57] ABSTRACT

A process for preparing substituted pyrimidine derivatives of the general formula (I):

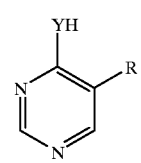

(I)

in which a [3-(dimethylamino)-2-azaprop-2-en-1-ylidine] dimethylammonium halide is reacted with a substituted acetamide. The compounds of general formula (I) are important intermediate products for pharmaceutical or agrochemical active substances.

15 Claims, No Drawings

PROCESS FOR PREPARING SUBSTITUTED PYRIMIDINE DERIVATIVES

This is a 371 PCT/EP98/00074, filed Jan. 8, 1998.

The invention relates to a novel way of obtaining substituted pyrimidine derivatives of the general formula

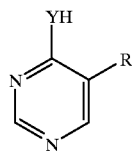

in which Y and R are as defined below. Said compounds have a very broad application spectrum, e.g. as intermediates for pharmaceutical or agrochemical active ingredients.

It is known to obtain compounds of the general formula I by reaction of tris-formaminomethane with CH acidic carboxamides (Brederbeck et al. Chem. Ber. 1965, 98, 3883–3887). The reaction mentioned by way of example is that of tris-formaminomethane with malonic acid ethyl ester amide in a yield of 11% to give the corresponding ethyl 4-hydroxypyrimidine-5-carboxylate (4-hydroxy-5-ethoxycarbonylpyrimidine).

Also known is the reaction of triazine for example with diethyl malonate in a yield of 42% to give ethyl 4-hydroxypyrimidine-5-carboxylate (Huffmann et al. J. Org. Chem. 1962, 27, 551–558).

These syntheses have the disadvantage that they firstly produce relatively poor yields, and secondly use starting compounds which are not readily available and are relatively expensive, thus making them uneconomical.

Consequently, the object of the invention was to develop a novel economic way of obtaining the compounds of the general formula I which does not have the said disadvantages.

The object was achieved with the process of the invention according to claim 1 or 5.

In the general formula I, Y is an oxygen atom or a sulphur atom. R is cyano or a group

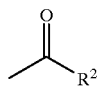

in which $R^2$ is optionally substituted alkyl, alkoxy, hydroxyl, amino, alkylamino, dialkylamino, phenyl or benzyl.

Alkyl expediently has the meaning of $C_{1-6}$-alkyl, such as methyl, ethyl, n-propyl, isopropyl, n-butyl, sec-butyl, tert-butyl, pentyl and its isomers or hexyl and its isomers, preferably $C_{1-4}$-alkyl. This definition of alkyl includes the alkyl radicals of alkoxy, alkylamino or dialkylamino. In addition, said radicals can be mono- or polysubstituted, by, for example, alkyl, alkoxy, amino or halogen. Halogen is customarily fluorine, chlorine, bromine or iodine, preferably chlorine or bromine.

The starting material in the process of the invention according to the variant as in claim 1 is [3-(dimethylamino)-2-azaprop-2-en-1-ylidene]dimethylammonium halide of the general formula

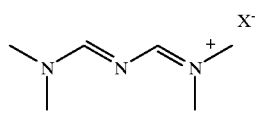

in which X is a halogen atom. This compound is known in the form of its chloride as "Gold's reagent". Gold's reagent is prepared in a known manner by reacting cyanuric chloride with N,N-dimethylformamide as in H. Gold, Angew. Chem. 1960, 72, 956–959.

Alternatively, as in claim 5, the Gold's reagent or another halide of the general formula II can be formed in situ and used for the subsequent stage without isolation.

A preferred [3-(dimethylamino)-2-azaprop-2-en-1-ylidene]dimethylammonium halide of the general formula II is "Gold's reagent" or [3-(dimethylamino)-2-azaprop-2-en-1-ylidene]dimethylammonium chloride.

The reaction of the invention with the compound of the general formula II is carried out with a compound of the general formula

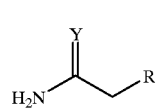

in which Y and R are as defined above.

Suitable compounds of the general formula III are the substituted acetamides in which Y is oxygen, and R is

Consequently, particular preference is given to malonamide or malonic acid $C_{1-6}$-alkyl ester manoamides, in particular malonic acid $C_{1-4}$-alkyl ester monoamides.

Other suitable compounds of the general formula III are cyanoacetamide and 2-cyanothioacetamide where R is cyano and Y is oxygen or sulphur, respectively.

Gold's reagent or another halide of the general formula II can usually be used in stoichiometric amounts, but is preferably used in a slight excess relative to the compound of the general formula III.

The reaction proceeds in the presence of a base.

Preference is given to using a customary alkali metal alkoxide such as, for example, Na or K methoxide, ethoxide or tert-butoxide.

The reaction expediently takes place in the presence of an organic solvent such as, for example, dimethoxyethane, dioxane, tetrahydrofuran or methanol. The reaction temperature is usually chosen to be in the range between 20° C. and 100° C. The process is preferably carried out at reflux temperature.

After a reaction time of 1 h to 20 h, the resulting pyrimidine of the general formula I can be separated off from the reaction mixture in a simple manner, usually by filtration.

In the case where, in the resulting pyrimidine of the general formula I, R is an ester function, acidic or basic work-up can be used to obtain the corresponding pyrimidinecarboxylic acid in a simple manner. The process of the invention enables the substituted pyrimidine derivatives of the general formula I to be obtained in good yields of above 80%.

EXAMPLES

Example 1

Process for the Preparation of [3-(dimethylamino)-2-azaprop-2-en-1-ylidene]dimethylammonium chloride (Gold's Reagent)

Cyanuric chloride (46.67 g, 0.252 mol) was heated with N,N-dimethylformamide (121.33 g, 1.66 mol) in 250 ml of tert-butyl methyl ether over the course of from 30 to 40 min. An exothermic reaction then took place, and $CO_2$ gas was liberated over the course of from 1 to 2 hours. The reaction mixture was boiled overnight. After the reaction mixture had cooled, the title product was isolated by rapid filtration under a nitrogen atmosphere and washing with tert-butyl methyl ether. Drying in a desiccator gave the title product in a yield of from 112.15 g (90.7%) in the form of a pale yellow solid.

m.p.=103° C.

$^1$H NMR (DMSO$_{d6}$, 400 MHz)δ=3.2 (s, 6H); 3.27 (s, 6H); 8.62 (s, 2H).

Example 2a

Process for the Preparation of methyl 4-hydroxypyrimidine-5-carboxylate

Methyl oxalate (0.2 eq.) and malonomonoamide monomethyl ester (58.55 g, 0.50 mol) were added to an initial charge of sodium methoxide (279.4 g, 1.5 mol, 29% in methanol). 350 ml of dimethoxyethane were added. The solid Gold's reagent prepared as in Example 1 (89.35 g, 0.55 mol) was then added using a spatula. The suspension was then stirred at room temperature for 18 hours. The yellow suspension was poured on to an aqueous, ice-cold hydrochloric acid solution (2 eq. of HCl). Following filtration at pH 9–10, the moist sodium salt of the title product was taken up in HCl-saturated methanol, stirred for 15 min, filtered and dried. The yield of the title product in the form of its hydrochloride was 52.3 g (55%).

$^1$NMR (DMSO$_{d6}$, 400 Hz)δ=3.8 (s, 3H); 5.7–6.4(broad, 1H); 8.4 (s, 1H); 8.5 (s, 1H).

Example 2b

Process for the Preparation of 4-hydroxypyrimidine-5-carboxylic acid

The moist sodium salt of methyl 4-hydroxypyrimidine-5-carboxylate obtained as in Example 2a) was taken up in water/tetrahydrofuran=1:1, and 1.0 eq of LiOH.H$_2$O was added. Following hydrolysis of the ester over 3.5 hours at 0° C. and 2 hours at room temperature, most of the tetrahydrofuran was evaporated and, at 0° C., a pH of 3 was adjusted using eq. HCl solution. After about 45 minutes at 0° C., the title product was filtered off. Drying gave the acid in a yield of 3.55 g (78%).

$^1$H NMR (DSO$_{d6}$, 400 MHz)δ=8.6 (s, 1H); 8.7 (s, 1H); 11.8–14.7 (broad, 2H).

Example 3

Process for the Preparation of 4-hydroxypyrimidine-5-carboxamide

At room temperature, malonodiamide (10.75 g, 0.10 mol) was added to a sodium methoxide solution (55.88 g, 0.30 mol., 29% in methanol.), and the mixture was diluted with tetrahydrofuran. At room temperature, the Gold's reagent prepared as in Example 1 (18.0 g, 0.11 mol) was added, and argon was passed through for 24 hours in order to drive off the dimethylamine liberated. The pH was then adjusted to 7.4 using an aqueous hydrochloric acid solution, and most of the tetrahydrofuran was removed on a rotary evaporator. The resulting suspension was adjusted to pH=5.5 using eq. HCl and heated to reflux temperature. Water was then added again in order to bring everything into solution, then activated carbon was added and the mixture was stirred under reflux for a further 15 min. After slow cooling to room temperature, pale yellow crystals precipitated out, which, after filtration, were dried under reduced pressure at 40° C. to give the title product in a yield of 5.58 g (80%)

$^1$H NMR (DMSO$_{d6}$, 400 Hz)δ=7.7 (s, broad, 1H); 8.4 (s, 1H); 8.5–8.6(s, broad, 1H); 8.6 (s, 1H).

Example 4

Process for the Preparation of 5-cyanopyrimidinol

Cyanoacetamide (8.58 g, 0.10 mol) was added to an initial charge of sodium methoxide (54.02 g, 0.30 mol, 29% in methanol). 150 ml of dimethoxyethane were added. The solid Gold's reagent prepared as in Example 1 (18.08 g, 0.11 mol) was then added using a spatula. The suspension was then stirred overnight at room temperature. The yellow suspension was poured on to an aqueous, ice-cold hydrochloric acid solution (2 eq. of HCl) and adjusted to pH 5.5. After the organic solvents had been evaporated off, the product precipitated out of the aqueous phase. Digestion in water and subsequent filtration gave the title product in a yield of: 9.14 g (75%) in the form a yellow solid.

$^1$H NMR (DMSO$_{d6}$, 400 MHz)δ=8.2 (s, 1H); 8.3 (s, 1H).

Example 5

Process for the Preparation of 5-cyano-4-pyrimidinethiol

At room temperature, 2-cyanothioacetamide (4.5 g, 0.045 mol) was added to an initial charge of sodium methoxide (24.3 g, 0.1.35 mol, 29% in methanol). 100 ml of dimethoxyethane were added. The Gold's reagent prepared as in Example 1 (8.1 g, 0.050 mol) was then added, and the reaction mixture was stirred at room temperature for about 5 hours. The mixture was then heated briefly to 50° C. and left to stand at room temperature overnight. The dimethoxyethane was stripped off on a rotary evaporator, 20 ml of water were added, and then the reaction mixture was cooled in an ice bath. 30 ml of 2N eq. HCl solution were used to adjust the pH to 5.5. After renewed cooling, the solid which had precipitated out was filtered off, then washed with a small amount of cold water and dried at 40° C. in a vacuum drying cabinet to give the title product in a yield of 5.57 g (90.4%) in the form of an orange solid.

$^1$H NMR (DMSO$_{d6}$, 400 MHz)δ=8.42 (s, 1H); 8.48 (s, 1H).

What is claimed is:

1. Process for preparing substituted pyrimidine derivatives of formula:

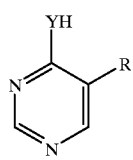

in which Y is an oxygen atom or a sulfur atom and R is cyano or is a group:

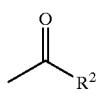

in which $R^2$ is unsubstituted or alkyl-, alkoxy-, amino- and/or halogen-substituted alkyl, alkoxy, hydroxyl, amino, alkylamino, dialkylamino, phenyl or benzyl, characterized in that a [3-(dimethylamino)-2-azaprop-2-en-1-ylidene] dimethylammonium halide of formula:

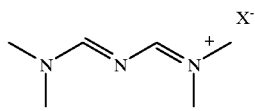

in which X is a halogen atom, is reacted in the presence of a base with a compound of the formula:

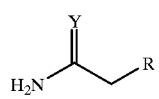

in which Y and R are as defined.

2. Process according to claim 1, characterized in that [3-(dimethylamino)-2-azaprop-2-en-1-ylidine] dimethylammonium chloride is used as the compound of the general formula II.

3. Process according to claim 2, characterized in that an alkali metal alkoxide is employed as the base.

4. Process according to claim 3, characterized in that the reaction is carried out in the presence of a solvent at a temperature between 20° C. and 100° C.

5. Process according to claim 1, characterized in that an alkali metal alkoxide is employed as the base.

6. Process according to claim 1, characterized in that the reaction is carried out in the presence of a solvent at a temperature between 20° C. and 100° C.

7. Process for preparing a substituted pyrimidine derivative of formula:

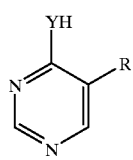

in which Y is an oxygen atom or a sulfur atom and R is cyano or is a group:

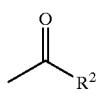

in which $R^2$ is unsubstituted or alkyl-, alkoxy-, amino- and/or halogen-substituted alkyl, alkoxy, hydroxyl, amino, alkylamino, dialkylamino, phenyl or benzyl, characterized in that, in a first stage, a cyanuric halide is converted with N,N-dimethylformamide into a [3-(dimethylamino)-2-azaprop-2-en-1-ylidene]dimethylammonium halide of formula:

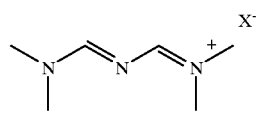

in which X is a halogen atom, and then, in the second stage, this product is reacted in the presence of a base with a compound of the formula:

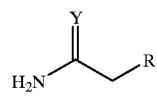

in which Y and R are as defined above.

8. Process according to claim 7, characterized in that [3-(dimethylamino)-2-azaprop-2-en-1-ylidine] dimethylammonium chloride is used as the compound of the general formula II.

9. Process according to claim 7, characterized in that the reaction in the first stage is carried out with cyanuric chloride.

10. Process according to claim 9, characterized in that an alkali metal alkoxide is employed as the base.

11. Process according to claim 10, characterized in that the reaction in the second stage is carried out in the presence of a solvent and at a temperature between 20° C. and 100° C.

12. Process according to claim 11, characterized in that the [3-(dimethylamino)-2-azaprop-2-en-1-ylidene] dimethylammonium halide resulting from the first stage is not isolated.

13. Process according to claim 7, characterized in that an alkali metal alkoxide is employed as the base.

14. Process according to claim 7, characterized in that the reaction in the second stage is carried out in the presence of a solvent and at a temperature between 20° C. and 100° C.

15. Process according to claim 7, characterized in that the [3-(dimethylamino)-2-azaprop-2-en-1-ylidine] dimethylammonium halide resulting from the first stage is not isolated.

* * * * *